United States Patent
Hodorek et al.

(10) Patent No.: US 8,632,603 B2
(45) Date of Patent: Jan. 21, 2014

(54) IMPLANT POSITIONING SYSTEMS FOR ORIENTING PROSTHESIS

(75) Inventors: Brian C. Hodorek, Winnona Lake, IN (US); Robert Courtney, Jr., Pierceton, IN (US); Ryan Schlotterback, Fort Wayne, IN (US)

(73) Assignee: Tornier, Inc., Edina, MN (US)

( * ) Notice: Subject to any disclaimer, the term of this patent is extended or adjusted under 35 U.S.C. 154(b) by 0 days.

(21) Appl. No.: 12/887,040

(22) Filed: Sep. 21, 2010

(65) Prior Publication Data

US 2012/0071985 A1 Mar. 22, 2012

(51) Int. Cl.
*A61F 2/28* (2006.01)

(52) U.S. Cl.
USPC .................. 623/23.27; 623/19.14; 623/23.25; 623/23.48

(58) Field of Classification Search
USPC ....................... 623/19.14, 23.25–23.27, 23.48
See application file for complete search history.

(56) References Cited

U.S. PATENT DOCUMENTS

| | | | |
|---|---|---|---|
| 5,078,746 A * | 1/1992 | Garner | 623/23.48 |
| 5,425,768 A * | 6/1995 | Carpenter et al. | 623/23.48 |
| 5,554,192 A | 9/1996 | Crowninshield | |
| 5,861,043 A * | 1/1999 | Carn | 623/23.48 |
| 5,885,295 A | 3/1999 | McDaniel et al. | |
| 6,217,620 B1 | 4/2001 | Park | |
| 7,749,279 B2 | 7/2010 | Twomey et al. | |
| 2001/0020187 A1 | 9/2001 | Guettinger et al. | |
| 2002/0095217 A1 * | 7/2002 | Masini | 623/22.12 |
| 2002/0128721 A1 * | 9/2002 | Chan | 623/23.48 |
| 2004/0107002 A1 * | 6/2004 | Katsuya | 623/23.25 |
| 2005/0246020 A1 | 11/2005 | Southworth | |
| 2008/0119861 A1 * | 5/2008 | Winslow et al. | 606/95 |

FOREIGN PATENT DOCUMENTS

| | | |
|---|---|---|
| EP | 0308081 B1 | 12/1991 |
| EP | 1419749 A1 | 5/2004 |
| EP | 2431008 A1 | 3/2012 |
| WO | WO9704723 A | 2/1997 |
| WO | WO9704723 A1 | 2/1997 |

OTHER PUBLICATIONS

Affiniti's Cortiloc Glenoid: A Leap Forward in Fixation, 2009 Tornier, Inc. product brochure, 3 pages.
European Search Report issued in EP Application No. 1181936, dated Dec. 23, 2011, 6 pages.

* cited by examiner

*Primary Examiner* — David Isabella
*Assistant Examiner* — Randy Shay
(74) *Attorney, Agent, or Firm* — Faegre Baker Daniels LLP (57) ABSTRACT

A system for securing a prosthesis in a bone includes a reference anchor for insertion into a cavity of a bone to define a reference point during prosthesis implantation, the reference anchor including a body having a mating feature and a gripping projection for engaging an inner surface of the bone cavity. The system also includes a stem having a terminal end adapted to mate with the engagement feature of the reference anchor such that the stem is disposed at a desired position relative to the reference point.

15 Claims, 7 Drawing Sheets

IMPLANT POSITIONING SYSTEMS FOR ORIENTING PROSTHESIS

BACKGROUND

Shoulder and other joint replacement techniques often require range of motion testing or other testing using a first, trial implant to initially evaluate a suitable position for the final implant. Generally, effective use of trial implants is dependent upon an ability to locate the final implant at substantially the same position and orientation as was used for the trial implant during evaluation. Often times, bone fractures or other damage impede use of boney landmarks or other bone features for implant positioning. For example, during shoulder replacement, proximal humerus fractures can impede a surgeon's ability to accurately position the final implant.

In typical humeral fractures, the proximal humerus breaks into two or three pieces, in what is called a three or four part fracture according to the Neer classification system. The broken pieces typically contain bony landmarks used to determine proper orientation and height for proper implantation of a humeral stem of a test and/or final implant. Therefore, a jig or other guide is needed to hold the trial implant during evaluation and then to hold the final implant. The final implant should generally replicate the same position of the trial implant, with a range of motion test being performed first on the trial implant and later the final implant. Generally, it is difficult to perform range of motion testing with jigs. Indeed, the jigs or guides are often moved, intentionally or inadvertently, in order to successfully perform range of motion testing, compromising replication of orientation and height from the trial implant to the final implant.

SUMMARY

Some embodiments relate to a system for securing a prosthesis in a bone. The system includes a reference anchor for insertion into a cavity of a bone to define a reference point during prosthesis implantation, the reference anchor including a body having a mating feature and a gripping projection for engaging an inner surface of the bone cavity. The system also includes a stem having a terminal end adapted to mate with the engagement feature of the reference anchor such that the stem is disposed at a desired position relative to the reference point.

Other embodiments relate to a reference anchor and test system. The system includes a reference anchor for deployment into a cavity of a bone to define a first reference point, the reference anchor including a body having a mating feature and an outer surface adapted to engage an inner surface of the bone cavity. A bone implant is adapted to be releasably connected to the reference anchor, the bone implant including a connector shaft having an elongate body extending from an actuation end to a coupling tip, the coupling tip being adapted to releasably mate with the mating feature of the reference anchor. The system also includes a stem having an inner lumen, the stem being adapted to be disposed within the bone cavity and to receive the connector shaft within the inner lumen such that the coupling tip is mated with the reference anchor.

Still other embodiments relate to a method of anchoring a prosthesis to a bone at a desired location. The method includes inserting a reference anchor in a bone cavity and orienting the reference anchor in the bone cavity using a connector shaft. A trial implant is inserted into the bone cavity and the trial implant is connected to the reference anchor. The method also includes verifying that the reference anchor is at a desired position using the trial implant and disconnecting the trial implant from the reference anchor. The prosthesis is inserted into the bone cavity and the prosthesis is secured to the reference anchor at the desired position.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

As previously noted, the drawings are to be regarded as illustrative in nature and not restrictive.

DETAILED DESCRIPTION

Various embodiments relate to a reference anchor that is deployable into a bone cavity to establish a reliable reference point from which to verify proper orientation and operation for a bone prosthesis using a trial implant and/or a bone prosthesis, such as an artificial humeral head. In some embodiments, the reference anchor is substantially bullet-shaped and is threaded, where the trial implant includes an elongate shaft, or rod, for driving, or screwing, the reference anchor into the bone canal (e.g., the medullary canal of a humerus). The reference anchor optionally includes a base with a recessed pocket for releasably connecting the reference anchor and the shaft of the trial implant (e.g., to remove the reference anchor from the bone cavity). The trial implant also includes one or more components that mimic or otherwise replicate an anticipated position of the prosthesis prior to final implantation thereof. Once an appropriate position for the reference anchor has been established and verified using the trial implant, the trial implant is disconnected from the reference anchor and the prosthesis is secured to the reference anchor. The reference anchor and prosthesis are optionally fixed in the bone cavity (e.g., using a bone cement). While some features and uses of various embodiments are provided above, a variety of additional and/or alternate features and uses are contemplated, as will be understood with reference to the remainder of the description.

Figure 1:
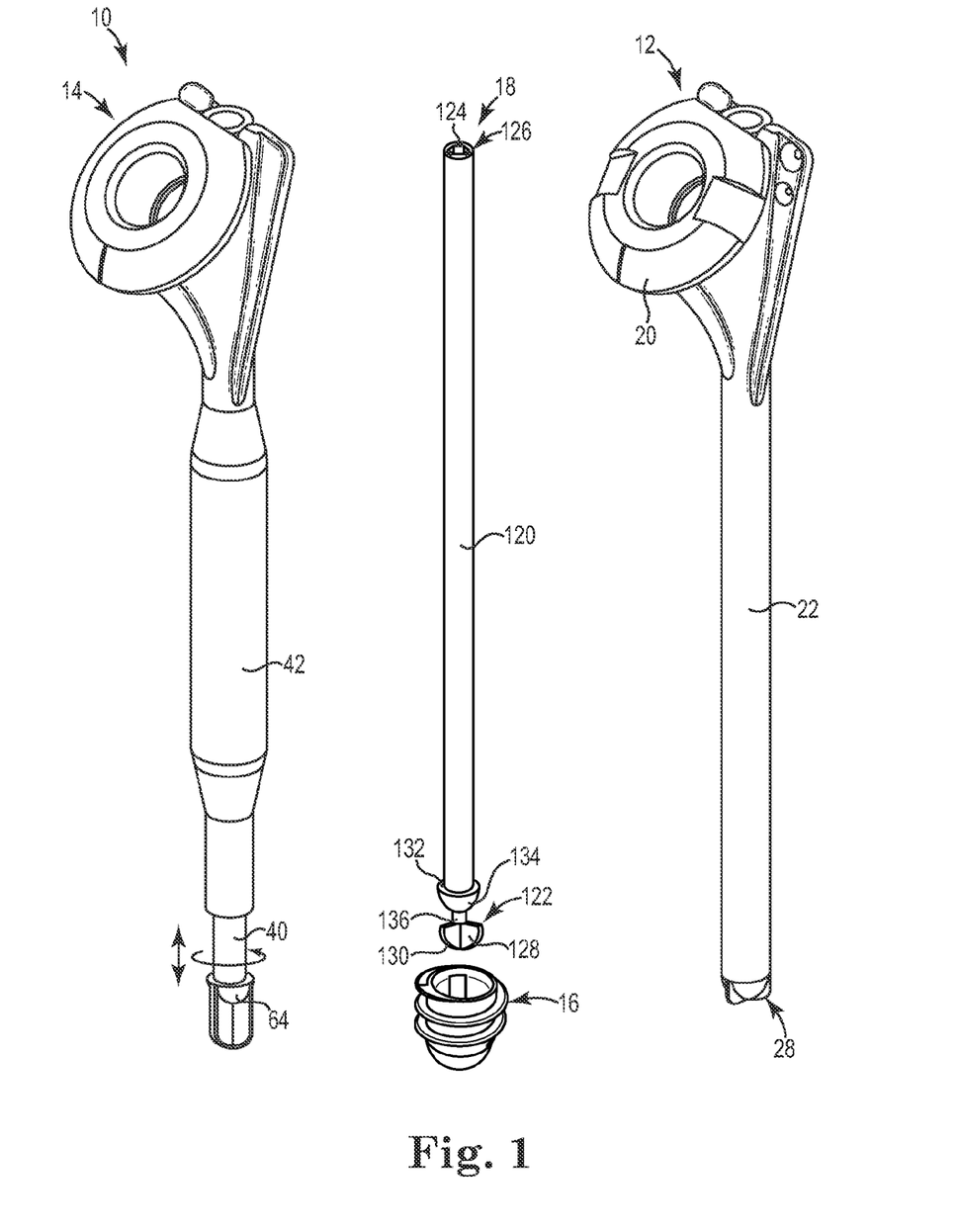
FIG. 1 shows a surgical system for prosthesis implantation in a bone cavity, according to some embodiments.

FIG. 1 shows a surgical system 10 including a prosthesis 12, a trial implant 14, a reference anchor 16 for use with the trial implant 14 and the prosthesis 12, and an interlocking connector shaft 18. In some embodiments, the prosthesis 12 is adapted to be implanted into the medullary canal in the humerus, although a variety of configurations are contemplated. For example, in other embodiments, the system 10 is adapted for implantation in a hip replacement procedure, with the prosthesis 12 being adapted for implantation into a femoral cavity.

As shown, the prosthesis 12 includes a prosthesis head 20 and a prosthesis stem 22. As shown, the prosthesis head 20 is similar to those of products sold under the trade names "AFFINITI" Shoulder System, though the prosthesis head 20 is optionally similar to those sold under the trade name "AEQUALIS" Fracture Shoulder, for example, both of which are provided by Tornier, Inc., having its U.S. headquarters in Minnesota. The prosthesis head 20 is adapted to receive and be connected to an artificial humeral head, such as those used in the AFFINITI and/or AEQUALIS systems. In other embodiments, the prosthesis head 20 is formed as an artificial humeral head, for example having a substantially smooth, convex articulation surface for direct contact with a glenoid or with an artificial glenoid component. As shown, the prosthesis stem 22 is substantially elongate and defines a terminal end 28. The prosthesis stem 22 is generally adapted to be inserted into a bone cavity, such as a proximal medullary canal of a humerus, where such bone cavities are often reamed or otherwise formed by a surgeon during a prosthesis implantation procedure.

Figure 2:
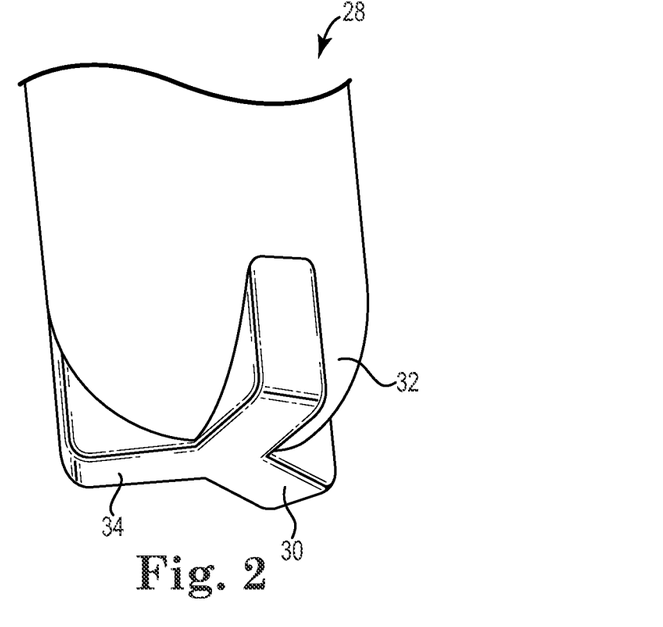
FIG. 2 is an isometric view of a terminal end of a prosthesis of the system of FIG. 1, according to some embodiments.
Figure 3:
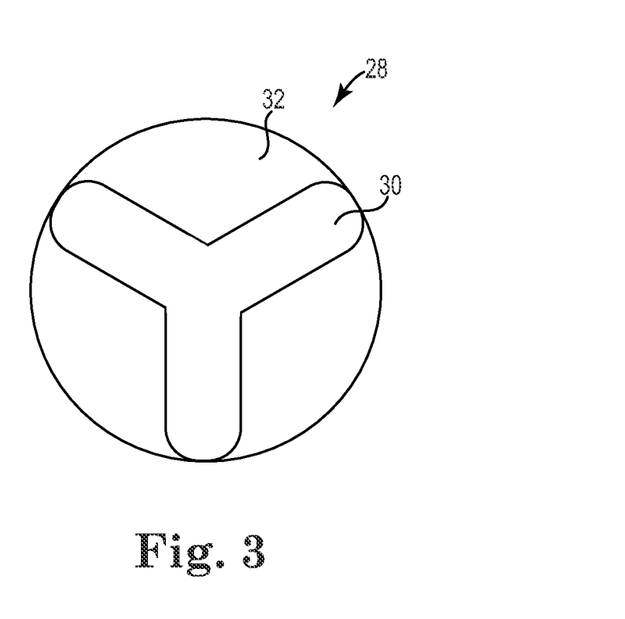
FIG. 3 is a bottom view of the terminal end of the prosthesis, according to some embodiments.

FIG. 2 is an enlarged isometric view of the terminal end 28 and FIG. 3 is an enlarged bottom view of the terminal end 28, according to some embodiments. As shown, the terminal end 28 is fluted, or includes a plurality of flanges 30, which serve as a means for aligning and mating the terminal end 28 to the reference anchor 16. The terminal end 28 also includes a hub 32 from which the flanges 30 extend, the hub 32 being substantially convex in shape. In some embodiments, the flanges 30 generally define a Y-shape when viewed from the bottom, with three flanges 30 each offset approximately 120 degrees from an adjacent one of the flanges 30, although a variety of configurations (X- or T-shaped for example), are contemplated. In some embodiments, the flanges 30 form a distal tip 34 of the terminal end 28 that has a rounded off profile (e.g., each of the flanges 30 is rounded distally along with the convex shape of the hub 32) to facilitate insertion into and seating with the reference anchor 16.

Figure 4:
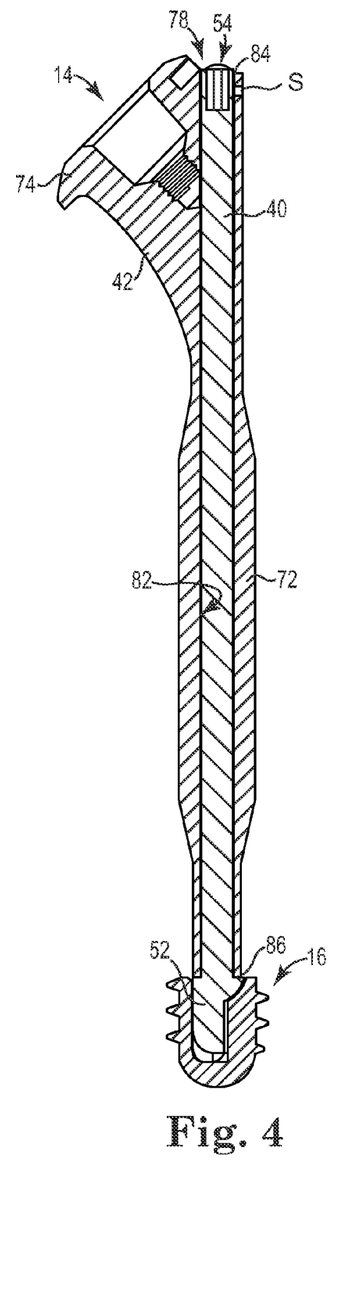
FIG. 4 is sectional view taken along a longitudinal axis of a trial implant of the system of FIG. 1, according to some embodiments.

FIG. 4 shows a longitudinal cross-section of the trial implant 14 aligned with the reference anchor 16, according to some embodiments. As shown, the trial implant 14 includes a connector shaft 40 and a test component 42, the connector shaft 40 being rotatably received in the test component 42. The connector shaft 40 is optionally longitudinally slidable in the test component 42 according to some embodiments and is longitudinally fixed in the test component 42 according to others. As indicated in FIG. 1, and as subsequently described, the connector shaft 40 is rotatably disposed in the test component 42.

Figure 5:
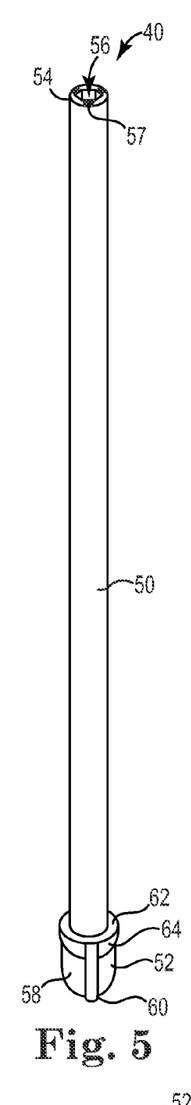
FIG. 5 is a perspective view of a connector shaft of the trial implant of FIG. 4, according to some embodiments.

FIG. 5 is an isometric view of the connector shaft 40, according to some embodiments. As shown, the connector shaft 40 has a body 50, or a rod portion, that is substantially elongate and a coupling tip 52 positioned distally on the body 50 and adapted to releasably mate with the reference anchor 16 for positioning the reference anchor 16 at a desired depth and orientation in the bone cavity. Proximally, the body 50 defines a drive end 54 that has a pocket 56, also described as a drive feature. In some embodiments, the pocket 56 is keyed to a male bit of a drill or other driver (e.g., the pocket and bit each having matching, hexagonal or other non-circular cross-sections). Additionally or alternatively, the outer periphery of the drive end 54 is optionally keyed, or non-circular (not shown) to mate with a female drill bit/driver. As shown, the drive end 54 includes alignment indicia 57 for aligning the connector shaft 40 to the test component 42, as subsequently described.

Figure 6:
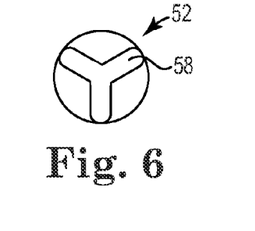
FIG. 6 is a bottom view of the connector shaft of FIG. 5, according to some embodiments.

FIG. 6 is an enlarged bottom view of the coupling tip 52, according to some embodiments. As shown in FIG. 6, the coupling tip 52 is fluted, or includes a plurality of flanges 58, also described as prongs or projections, which serve as a means for connecting coupling tip 52 to the reference anchor 16. In some embodiments, the flanges 58 generally define a Y-shape when viewed from the bottom, with three flanges 58 each offset approximately 120 degrees from an adjacent one of the flanges 58, although a variety of configurations are contemplated (e.g., X-shaped or T-shaped flange arrangements). As shown in FIG. 5, the flanges 58 form a distal tip 60 that is rounded to facilitate insertion into, and seating with the reference anchor 16. In some embodiments, the coupling tip 52 also includes a shoulder 62 and a substantially convex hub 64.

Figure 7:
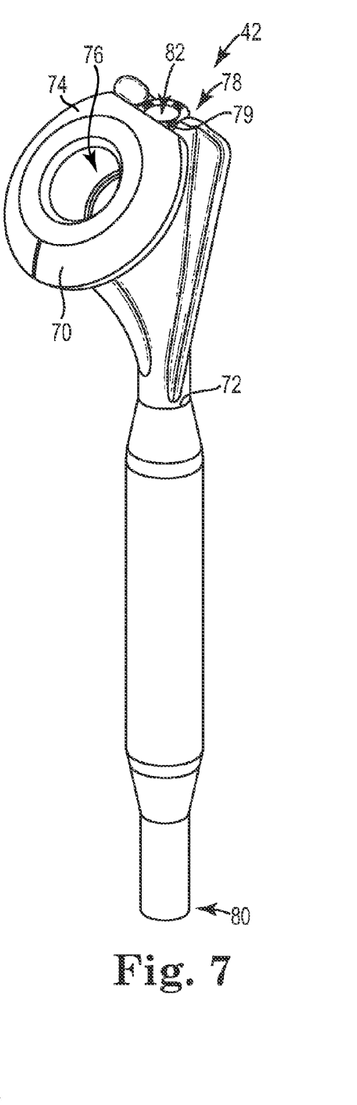
FIG. 7 is an isometric view of a test component of the trial implant of FIG. 4, according to some embodiments.

FIG. 7 is an isometric view of the test component 42, according to some embodiments. As shown, the test component 42 includes a test head 70 and a test stem 72 that is substantially elongate. The test head 70 projects angularly from the test stem 72 and has a support surface 74 and a receptacle 76 which, as shown, are adapted for receiving an artificial humeral head such as those previously described, though the test head 70 is optionally adapted to receive other components, such as an artificial femoral head, for example.

As shown, the test stem 72 defines a proximal end 78 and a distal end 80 and includes an inner lumen 82 (FIG. 4). At the proximal end 78, the test stem 72 has a plurality of alignment demarcations 79 which match the demarcations 57 on the connector shaft 40, according to some embodiments. The test stem 72 is adapted to be disposed within the bone cavity, such as a proximal medullary canal of a humerus. The lumen 82 is sized to coaxially receive the connector shaft 40 such that the connector shaft 40 is able to rotate about the central longitudinal axis of the connector shaft 40. The lumen 82 extends from a first, proximal end 84 next to the test head 70 to a second, distal end 86 away from the test head 70.

As shown, the test head 70 is generally adapted to project from the bone (e.g., proximal an anatomical or a surgical neck of a humerus) with the test stem 72 disposed in the bone cavity. In particular, the test head 70 is optionally of a substantially similar size and/or shape as the prosthesis head 20 (FIG. 1), which helps facilitate evaluation of an appropriate size, orientation, and location of the prosthesis 12 in the bone cavity, as subsequently described. In some embodiments, the receptacle 76 is adapted to receive different artificial humeral head components (not shown) of different sizes, each with a male projection that is secured in the receptacle and allows a surgeon or other user to evaluate proper sizing for a final, artificial humeral head component to be used with the prosthesis 12.

As shown in FIG. 4, assembly of the trial implant 14 includes coaxially receiving the connector shaft 40 in the inner lumen 82 of the test component 42. In some embodiments, the connector shaft 40 is slid into the distal end 80 (FIG. 7) of the test stem 72 until the drive end 54, and particular, the pocket 56 is located at the proximal end 78 of the test stem 72. For example, in some embodiments, the length of the connector shaft 40 between the drive end 54 and the shoulder 62 (FIG. 5) of the coupling tip 52 is adapted such that the connector shaft 40 is inserted into the test stem 72 until the shoulder 62 contacts the distal end 80 of the stem 72, at which time a user is able, through tactile feel, to determine that the connector shaft 40 has been fully received in the test stem 72.

Figure 8:
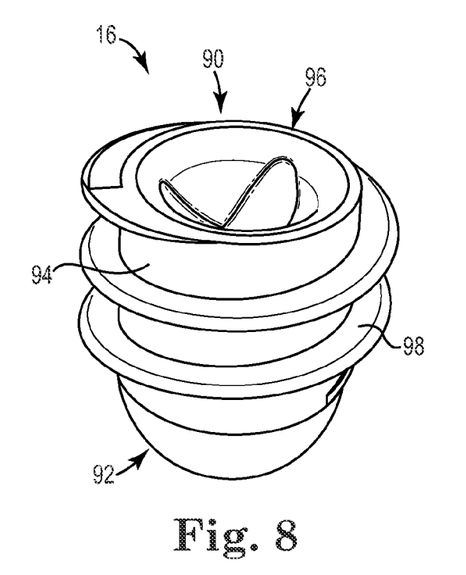
FIGS. 8 to 11 show a reference anchor of the system of FIG. 1, according to some embodiments.
Figure 9:
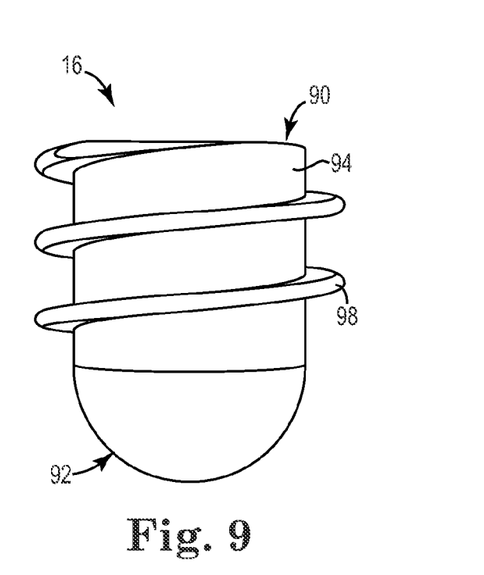
Figure 10:
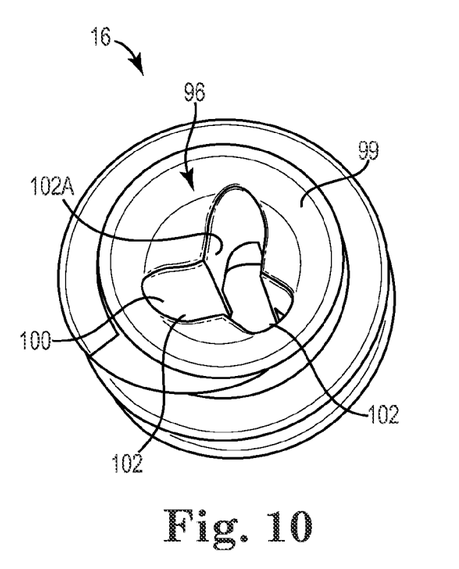
Figure 11:
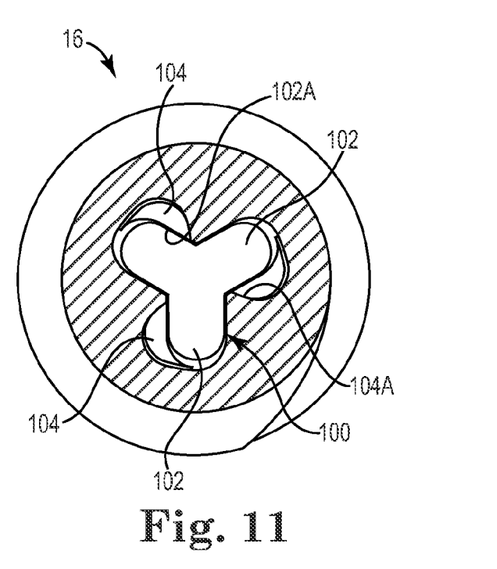

FIGS. 8 to 11 show the reference anchor 16, according to some embodiments, where FIG. 8 is an isometric view, FIG. 9 is a front view, FIG. 10 is a top view, and FIG. 11 is a cross-sectional view taken along line 11-11 in FIG. 9. As shown in FIGS. 8 and 9, the reference anchor 16 is substantially bullet-shaped, having a body that is substantially cylindrical and a nose that tapers, or narrows in diameter and is substantially rounded. The reference anchor defines a proximal end 90, a distal end 92, an outer surface 94, and a pocket 96. The reference anchor 16 also includes a gripping projection 98 in the form of male threading about the outer surface 94. In some embodiments, the gripping projection 98 and/or the body of the reference anchor 16 is substantially compliant (e.g., to reduce hoop stresses on the bone as the reference anchor 16 is driven into the bone cavity, to flexibly engage inner surfaces of the bone cavity. For example, the gripping projection 98 and/or other portions of the reference anchor 16 are optionally formed of UHMWPE "GUR" 1050, which is sufficiently soft and/or pliable to conform to the walls of the bone cavity, although other materials are contemplated. For example, the gripping projection 98 optionally formed of biocompatible, polymeric materials having a modulus of elasticity of about 700 MPa or less, 600 MPa or less, or about 550 MPa or less.

As shown in FIGS. 8 and 10, the pocket 96 has a concave portion 99, or bowl-shaped portion, and a mating portion 100, also described as a mating feature or a female mating feature, including a plurality of florets 102 (also described as segments or sections) bounded by floret walls 102A, the florets 102 being substantially complementary in configuration to the flanges 30 of the prosthesis 12 and the flanges 58 of the connector shaft 40. For example, three florets 102 are shown, each floret 102 being offset about 120 degrees from an adjacent one of the florets 102, although a variety of configurations are contemplated. As shown in upward looking cross-sectional view of FIG. 11, the mating portion 100 also includes a plurality of undercuts 104 bounded by undercut walls 104A, the undercuts 104 being skewed, or rotated relative to the florets 102. As subsequently described, the undercuts 104 are optionally used to interlock the reference anchor 16 with the interlocking connector shaft 18 such that the interlocking connector shaft 18 is able to be used to longitudinally pull on the reference anchor 16 (e.g., in order to help remove and/or insert the reference anchor 16 from the bone cavity).

The interlocking connector shaft 18 is shown from an isometric view in FIG. 1, according to some embodiments. As shown, the interlocking connector shaft 18 includes a body 120, or a rod portion, that is substantially elongate and a coupling tip 122 positioned distally on the body 120 and adapted to releasably mate with the reference anchor 16 for positioning the reference anchor 16 at a desired depth and orientation in the bone cavity. Proximally, the body 120 defines a drive end 124 that has a pocket 126. In some embodiments, the pocket 126 is keyed to a male bit of a drill or other driver (e.g., the pocket and bit having matching, hexagonal or other non-circular cross-sections). Additionally or alternatively, the outer periphery of the drive end 124 is optionally keyed, or non-circular (not shown) to mate with a female drill bit/driver.

As shown, the coupling tip 122 is fluted, or includes a plurality of flanges 128, also described as prongs or projections, which serve as a means for connecting coupling tip 122 to the reference anchor 16. In some embodiments, the flanges 128 generally define a Y-shape when viewed from the bottom, with three flanges 128 each offset approximately 120 degrees from an adjacent one of the flanges 128, although a variety of configurations are contemplated (e.g., X-shaped or T-shaped flange arrangements). In some embodiments, the flanges 128 form a distal tip 130 that is rounded to facilitate insertion into the reference anchor 16. As shown, the coupling tip 122 also includes a shoulder 132 and a substantially convex hub 134 with an intermediate member 136 extending between the hub 134 and the flanges 128.

Figure 12:
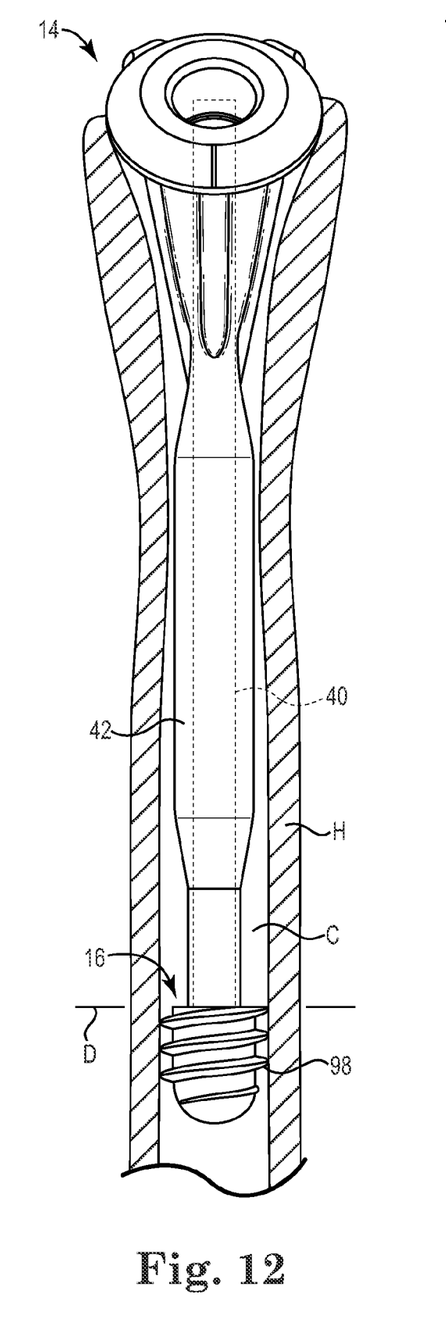
FIG. 12 shows the trial implant and reference anchor of the system of FIG. 1 positioned in a bone cavity, according to some embodiments.

With reference to FIG. 12, some methods of implantation into a bone cavity C using the system 10 include reaming or otherwise forming the bone cavity, such as reaming out a proximal medullary canal of a humerus H. The reference anchor 16 is inserted in the bone cavity C and oriented using the connector shaft 40 (FIG. 5) and/or the interlocking connector shaft 18 (FIG. 1). For example, the coupling tip 52 of the connector shaft 40 is optionally inserted into the pocket 96 of the reference anchor 16, where the flanges 58 are received into the florets 102 in a complementary fit and the hub 32 is received against the bowl-shaped portion 99 in a complementary fit. Once connected to the reference anchor 16, rotation of the connector shaft 40 results in rotational movement of the reference anchor 16. In some embodiments, the connector shaft 40 forms a friction fit with the reference anchor 16 to help reduce the potential for the reference anchor 16 to inadvertently disconnect from the connector shaft 40.

The test component 42 (FIG. 4) is optionally received over the connector shaft 40 prior to advancing the reference anchor 16. In other words, the trial implant 14 is preassembled prior to driving the reference anchor 16 into the cavity. In other embodiments, the connector shaft 40 is first used to drive the reference anchor 16 to a desired depth in the bone cavity and the test component 42 is subsequently assembled over the connector shaft 40. Regardless, in some embodiments, a driver (such as a drill) engaged with the drive end 54 of the connector shaft 40 is used to rotate the reference anchor 16, which, in turn, causes the reference anchor 16 to descend into the bone cavity. In particular, the gripping projection 98 frictionally and/or mechanically threads down the cavity to assist with locating the reference anchor 16 at the desired depth.

As shown in FIG. 12, the reference anchor 16 is deployed to a desired depth D in a bone cavity C of a humerus H. In one embodiment, the cavity C is prepared to a 10 mm diameter (e.g., using a reamer) where the major diameter of the reference anchor 16 (i.e., at the outermost profile of the threads) is 12 mm to provide about 1 mm of interference around the reference anchor 16, although a variety of dimensions are contemplated. For example, in some embodiments the cavity C is reamed to a diameter where a majority of the bone forming the cavity C is cortical bone rather than softer, cancellous bone such that less or substantially no threading of the gripping projection 98 into the bone occurs. In other embodiments, the cavity C is reamed to allow for such threading, for example where additional, mechanical engagement between the bone and the reference anchor 16 is desired.

In some embodiments, the evaluation process includes receiving the test component 42 over the connector shaft 40, driving the reference anchor 16, and thus, the trial implant 14, to a desired depth, and determining a rotational orientation of the test component 42 relative to the reference anchor 16. For example, the test component 42 is coaxially disposed over the connector shaft 40 (shown in broken lines) such that the shoulder 62 (FIG. 5) abuts the distal end 80 of the test component 42. The rotational orientation of the reference anchor 16 (including the relative, rotational orientation of the florets 102) and the depth D of the reference anchor 16 defines a reference point, also described as an anchor point, from which performance of the trial implant 14 and/or prosthesis 12 can be evaluated. For example, once positioned as desired, the reference anchor 16 preferably has substantial holding power to allow range of motion testing using the test component 42 and/or the prosthesis 12, as subsequently described.

Figure 13:
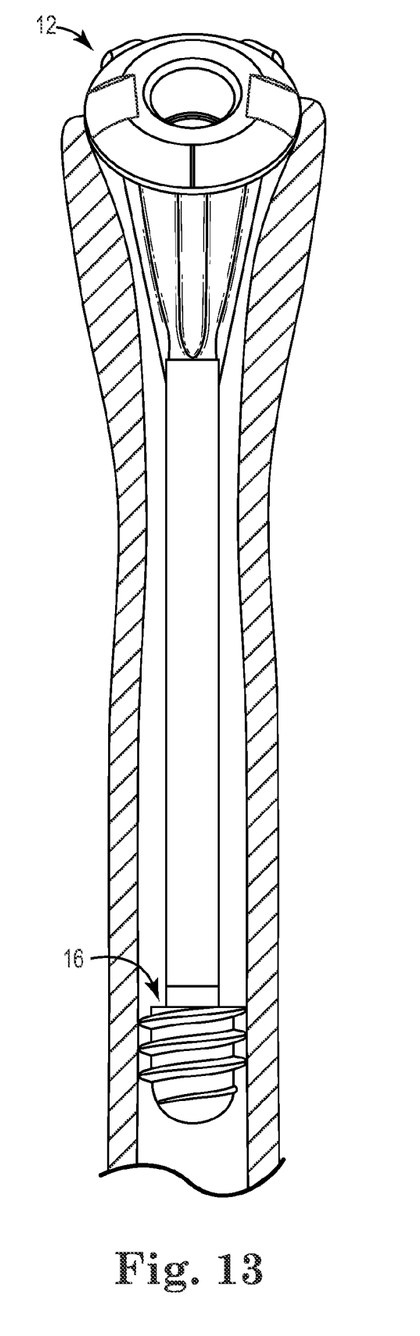
FIG. 13 shows the prosthesis and reference anchor of the system of FIG. 1 positioned in a bone cavity, according to some embodiments.

In some embodiments, the rotational orientation and depth D of the reference anchor 16 is evaluated using the test component 42 and, once the test component 42 is determined to be at an acceptable position, the test component 42 is disconnected from the reference anchor 16 and the prosthesis 12 is secured to the reference anchor 16 for final implantation as shown in FIG. 13. In some embodiments, the connector shaft 40 is rotated into a known rotational alignment with the reference anchor 16 by aligning the demarcations 79 at the proximal end 78 of the test component 42 to the demarcations 57 at the drive end 54 of the connector shaft 40. The rotational position, or orientation, of the test component 42 is evaluated along with the depth at which the test component 42 is positioned, the orientation and depth being adjusted as desired while maintaining the alignment of the demarcations 57, 79 to help ensure that the rotational orientation of the reference anchor 16 is known. Although visual demarcations are optionally used for rotational alignment between the connector shaft 40 and the test component 42 (and thus between the test component 42 and the reference anchor 16), tactile demarcations (e.g., detents that allow the user to feel when the connector shaft 40 and the test component 42 are aligned) are also contemplated.

In some embodiments, once the reference anchor 16 is initially believed properly oriented and located, or close thereto, the surgeon or other user makes an initial determination whether the test component 42 is at an appropriate location for range of motion (ROM) or other testing of the test component 42. If the test component 42 is determined to be misaligned with the bone, or at an inappropriate depth, the reference anchor 16 is rotated using the connector shaft 40 and the position of the test component 42 is reevaluated.

Once an initial position is determined to be acceptable, a set screw S is optionally received in the test component 42 such that the set screw S is able to be screwed inward to engage the connector shaft 40 to rigidly lock the test component 42 and the connector shaft 40 together. As shown, the set screw S is located on a proximal portion of the test component 42, although other locations are contemplated. In some embodiments, the set screw S is used to secure the connector shaft 40 relative to the test component 42 for range of motion testing or other evaluation. For example, in a shoulder prosthetic application, an artificial humeral head (not shown) is optionally secured to the test head 70 of the test component 42 with the surgeon performing various evaluations on the sizing, shape, and/or position of the test component 42 and the artificial humeral head. If the surgeon decides to adjust a depth or orientation of the test component 42, the set screw (not shown) is loosened and the reference anchor 16 is adjusted using the connector shaft 40, with further evaluation performed as desired.

In some embodiments, the surgeon may wish to remove the reference anchor 16 from the cavity C. For example, the reference anchor 16 may have too small or too large of an effective diameter, the surgeon may wish to further form the cavity C, or other considerations may warrant removal of the reference anchor 16. Where removal is desired, the reference anchor 16 may be overly loose in the cavity C, making it difficult to back drive the reference anchor 16 from the cavity C using the gripping projection 98 or other factors may make it difficult to remove the reference anchor 16. Regardless, in some embodiments, the interlocking connector shaft 18 is employed to facilitate removal of the reference anchor 16, as subsequently described. Alternatively, in some embodiments, the interlocking connector shaft 18 is used throughout implantation in lieu of the connector shaft 40.

In some embodiments, the interlocking connector shaft 18 (FIG. 1) is inserted into the reference anchor 16 such that the flanges 128 are received in the florets 102 (FIG. 11) of the reference anchor 16. In some embodiments, the concave portion 99 (FIG. 10), rounded edges of the florets 102, and/or rounded edges of the flanges 128 provide self-centering means for aligning the florets 102 and the flanges 128. In some embodiments, the shaft 18 is advanced until the convex hub 134 is seated against the concave portion 99 of the reference anchor 16. As the interlocking connector shaft 18 is advanced, the flanges 128 are positioned adjacent the open spaces corresponding to the undercuts 104 with the flanges 128 engaging the floret walls 102A for drive rotation, or forward rotation as desired.

In some embodiments, upon back-rotating the interlocking connector shaft 18 (e.g., in a counter clockwise direction), the flanges 128 angulate into position into the undercuts 104 (FIG. 11), which axially, or longitudinally locks the connector shaft 18 and the reference anchor 16 together. This axial interlocking means, or axial locking feature, helps the surgeon pull axially on the reference anchor 16, along the long axis of the cavity C, to remove the reference anchor 16 from and/or insert the reference anchor 16 into the cavity C.

Once the surgeon desires to unlock the interlocking connector shaft 18 from the reference anchor 16, the surgeon rotates the interlocking connector shaft 18 in the drive direction (e.g., a clockwise direction), which moves the flanges 128 out from the undercuts 104, in turn unlocking the connector shaft 18 from the reference anchor 16 longitudinally, or axially, while still interlocking the reference anchor and the connector shaft rotationally, with the flanges 128 engaging the undercut walls 104A (FIG. 11). This selective axial locking feature helps allow a surgeon to axially lock the two components by back rotation and axially unlock the two components by forward rotation of the interlocking connector shaft 18. Moreover, in the unlocked position the components 16, 18 are still rotationally locked for driving the reference anchor 16 and, in turn, in the unlocked position the two components 16, 18 are still rotationally locked for back rotating the reference anchor 16.

While embodiments have been shown and described with a set of undercuts 104 in the back drive direction only, it is also contemplated that an alternate or additional set of undercuts 104 is optionally formed in the drive direction, facilitating axial locking in the drive, or forward rotational direction as well as or instead of the backward rotational direction.

Upon determining that the reference anchor 16 is positioned as desired—for example, where it has been determined that the test component 42 is performing as desired, the test component 42 and connector shaft 40 (or connector shaft 18 as appropriate) are disconnected from the reference anchor 16 and the prosthesis 12 is connected to the reference anchor 16.

While, in some embodiments, the test component 42 is used to evaluate positioning of the reference anchor 16 and/or an appropriate size and configuration for the prosthesis 12, in other embodiments, the reference anchor 16 is implanted into the cavity C at the desired position using different methodology. For example, fluoroscopic guidance is optionally used to position the reference anchor 16, with the reference anchor 16 and/or the connector shaft 40 including radiopaque markings and/or material.

In some embodiments, the prosthesis 12 is inserted into the bone cavity C and aligned to the reference anchor 16, with the concave portion 99, rounded edges of the florets 102, and/or rounded off profile of the terminal end 28 providing self-centering means between the prosthesis 12 and the reference anchor 16. If desired, the reference anchor 16 and the prosthesis 12 are mated together and then tested using range of motion testing to check that the reference anchor 16 has been accurately positioned. As previously referenced, by orienting the reference anchor 16 at a known, desired rotational orientation, for example using the demarcations 57, 79 (FIGS. 5 and 7), the prosthesis 12 is automatically oriented at the desired rotational orientation as the flanges 30 are configured similarly to the flanges 58 of the connector shaft 40 and/or flanges 128 of the interlocking connector shaft 18. In particular, the surgeon need only be close, on a gross scale, to the proper rotational orientation with the florets 102 of the reference anchor 16 then guiding the prosthesis 12 to the proper orientation.

During insertion of the prosthesis into the reference anchor 16, in some embodiments, the terminal end 28 of the prosthesis 12 is adapted such that the flanges 58 do not bottom out in the florets 102, leaving a substantial space in the florets 102 below the flanges 58. For example, bone cement (not shown) and/or other fixation material is injected into the cavity C for prosthesis implantation. The prosthesis 12 is inserted into the cavity C displacing some of this fixation material. By leaving space in the florets 102 under the flanges 58, the system 10 helps better ensure that the fixation material will have room to escape and the prosthesis 12 will be fully seated against the reference anchor 16, with the substantially convex hub 64 engaging the concave portion 99 of the pocket 96 and the prosthesis 12 secured to the reference anchor 16 at the desired position. Additionally or alternatively, the fixation material is optionally injected or otherwise inserted into the bone cavity C during initial positioning of the reference anchor 16 and/or prior to evaluation using the trial implant 14. For example, though not necessarily requisite, the coupling tips 52, 122 are optionally designed to leave some space or play below them in the pocket 96 to allow for some displacement of fixation material.

Figure 14:
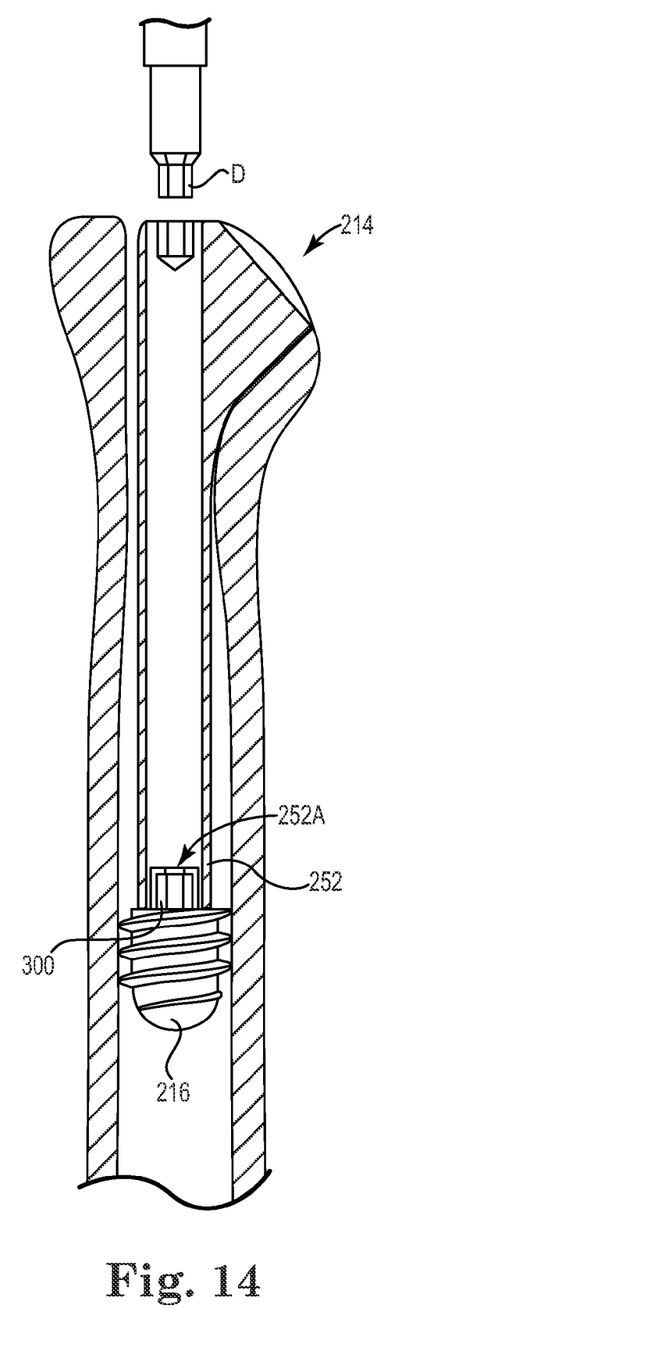
FIG. 14 shows another trial implant and reference anchor being positioned in a bone cavity, according to some embodiments.

While various connections have been described between the reference anchor 16 and the connector shaft 40 and interlocking connector shaft 18 in a male-female relationship, it is also contemplated that the male-female features are optionally reversed on the components. For example, FIG. 14 shows a driver bit D to be used with a trial implant 214, where the trial implant 214 has a coupling tip 252 with a female receptacle 252A (e.g., a hex receptacle) and a reference anchor 216 with a mating portion 300, or mating feature, that is a male connector (e.g., a hex projection), according to some embodiments. As show, the coupling tip 252 of the trial implant 214 is adapted to receive the mating portion 300 of the reference anchor 216.

Additionally, while the prosthesis 12 is described as having a prosthesis head 20 and a prosthesis stem 22, in other embodiments, the prosthesis to be implanted and/or the trial implant to be used for evaluation and positioning of the reference anchor 16 includes a stem portion without a larger, head portion that protrudes from the bone. For example, as shown in FIG. 15, the prosthesis 12 and/or trial implant 14 is optionally configured as a nail component (e.g., a medullary nail).

Figures 15, 16, 17, 18:
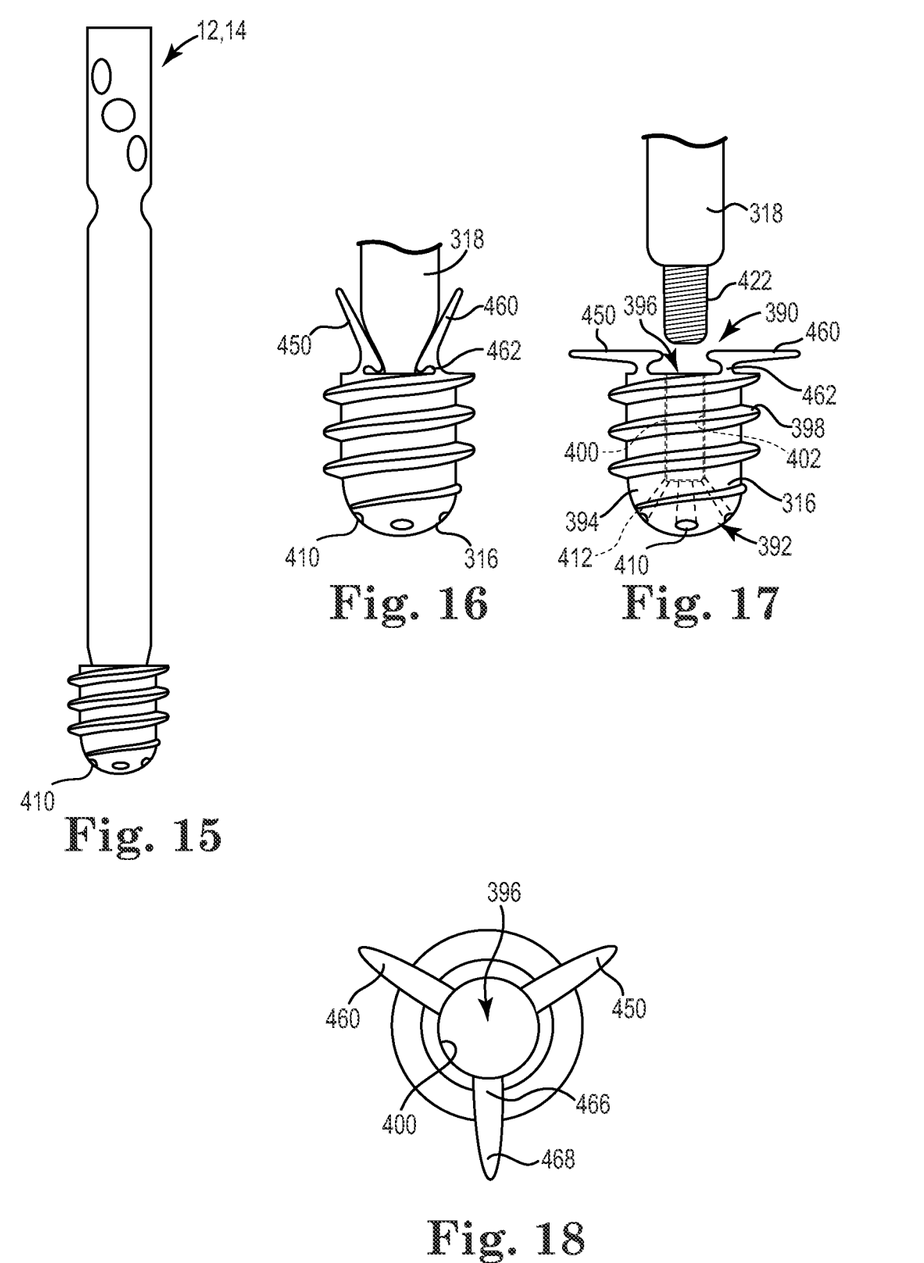
FIG. 15 shows another prosthesis, according to some embodiments.
FIGS. 16 to 18 show another reference anchor, according to some embodiments.

FIGS. 16 and 17 illustrate another reference anchor 316 and interlocking shaft 318, according to some embodiments. The interlocking shaft 318 optionally corresponds to a removal tool, a trial implant, or a prosthesis shaft as desired. As shown in FIG. 17, a coupling tip 422 of the interlocking shaft 318 includes male threading (the reference anchor 316 including complementary, female threading), which provides interlocking and mating means for connecting the two components 316, 318 rotationally and axially locking the two components 316, 318 during forward driving rotation (e.g., clockwise rotation that helps the reference anchor 316 pull itself deeper into a bone cavity).

In some embodiments, the reference anchor 316 is similar to the reference anchor 16. As shown, the reference anchor 316 defines a proximal end 390, a distal end 392, an outer surface 394, and a pocket 396. The reference anchor 316 includes a gripping projection 398 in the form of male threading about an outer surface 394 of the reference anchor 316. The reference anchor 316 is substantially bullet-shaped, having a body that is substantially cylindrical and a nose that tapers, or narrows in diameter. As indicated, the pocket 396 defines a mating portion 400, also described as a mating feature or a female mating feature, including internal threading 402 (indicated by dotted lines) that is substantially complementary to the threading of the prosthesis/connector shaft configuration. As shown, the reference anchor 316 also includes one or more secondary gripping projections 450 that are selectively deployable using the interlocking shaft 318.

As shown in FIGS. 15-17, the reference anchor 316 includes a plurality of openings 410 at the distal end 392 of the reference anchor 316. As shown in FIG. 17, each of the plurality of openings 410 is connected to the pocket 396 by a channel 412. In some embodiments, bone cement or other material is able to be pressed from the pocket 396 out of the openings 410. For example, the openings 410 are optionally used to allow displacement of additional bone cement from the pocket 396 as the prosthesis 12 is being inserted into the pocket 396. Additionally or alternatively, the prosthesis 12 and/or the trial implant 14 are optionally configured to inject bone cement, or other material (e.g., drugs, biologic material, stem cells, bone marrow, or others), into the pocket 396 and out from the openings 410 for delivering bone cement, or other material, under and/or around the reference anchor 316. Though the openings 410 are shown at the distal end 392, additional or alternate positions are contemplated, including openings along the entire body toward the proximal end 390. As another option, the body of the reference anchor 316 is optionally formed of a porous material that facilitates material flow out of the pocket 396 and from the reference anchor 316.

The plurality of gripping projections 450 shown in FIGS. 16 and 17 are secured to a remainder of the reference anchor 316 at the proximal end 390. The gripping projections 450 each include an arm 460 and a connection 462, also described as a fulcrum, where the arm 460 is hinged to a main body 464 of the reference anchor 316. FIG. 18 is a top view of the reference anchor 316. As shown, the arms 460 define a base portion 466 inwardly, toward a central longitudinal axis of the reference anchor 316 and a contact portion 468 away from the central longitudinal axis of the reference anchor 316.

As shown in FIGS. 17 and 19, the arms 460 are biased to an unfolded configuration in a position that is substantially orthogonal to the central longitudinal axis of the reference anchor 316, extending away from the central longitudinal axis of the reference anchor 316. Once the interlocking shaft 318 is inserted into the pocket 396, the interlocking shaft 318 contacts the base portions 466 of the arms 460 and hinges, or swings the arms 460 to a more compact configuration as shown in FIG. 16, with the arms 460 extending more parallel to the central longitudinal axis of the reference anchor 316. In other words, the reference anchor 316 defines a smaller effective diameter when attached to the interlocking shaft 318.

In some embodiments, the interlocking shaft 318 is connected to the reference anchor 316 and the reference anchor 316 is driven (e.g., rotated to engage the external threading with sidewalls of a bone cavity such that the reference anchor 316 pulls itself into the cavity) or otherwise positioned in the bone cavity. Once positioned, the interlocking shaft 318 is freed from the reference anchor 316, causing the gripping projections 450 to splay outwardly against the cavity wall, thereby helping secure the anchor 316 in the bone cavity. In some embodiments, the gripping projections 450 are substantially compliant, for example being made of similar materials to those previously described, to reduce the potential for damage to the bone cavity, including hoop stresses on the surrounding bone.

A variety of modifications and additional or alternative features are contemplated. For example, in some embodiments, the interlocking connecting shaft 18 is provided with flanges that grip the inside of the reference anchor 16, for example. Moreover, while some features have been described in association with various embodiments, any combination of features between the various embodiments is contemplated. In other words, various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. A system for securing a prosthesis in a bone, the system comprising:
    a reference anchor for insertion into a cavity of a bone to define a reference point during prosthesis implantation, the reference anchor including a body having a mating feature and a gripping projection for engaging an inner surface of the bone cavity; wherein the mating feature is configured to mate with a connector shaft in at least one discrete rotational orientation such that rotation of the connector shaft rotates the reference anchor into the bone cavity to facilitate positioning the mating feature in a desired rotational orientation in the bone cavity; and
    a stem having a terminal end adapted to mate with the mating feature of the reference anchor in the at least one discrete rotational orientation such that the stem is disposed in the desired rotational orientation in the bone cavity, wherein the stem is a prosthetic stem adapted for implantation.

2. The system of claim 1, wherein the gripping projection includes external threads for engaging the inner surface of the bone cavity.

3. The system of claim 1, wherein the reference anchor is adapted to be transitioned from a first, collapsed state to a second, expanded state to increase in effective diameter.

4. The system of claim 1, wherein the outer surface of the reference anchor is adapted to flexibly engage an inner surface.

5. The system of claim 1, wherein the mating feature of the reference anchor includes a receptacle for receiving the terminal end of the stem.

6. The system of claim 1, wherein the mating feature of the reference anchor includes a receptacle forming an undercut portion for releasably securing the stem in the receptacle.

7. The system of claim 1, further comprising a trial implant comprising the connector shaft including an elongate body having a coupling tip adapted to releasably mate with the mating feature of the reference anchor for positioning the reference anchor at a desired depth and the desired rotational orientation in the bone cavity.

8. The system of claim 7, wherein the trial implant further comprises a test component including a test head and a test stem having an inner lumen, the test stem being adapted to be disposed within the bone cavity and to receive the connector shaft within the inner lumen and the test head being adapted to project from the bone for evaluating the desired position of the prosthesis.

9. The system of claim 8, wherein the test stem is adapted to be disposed in a medullary canal of a humerus.

10. The system of claim 8, wherein the connector shaft is rotatably disposed in the inner lumen of the test stem.

11. The system of claim 8, wherein the connector shaft defines a drive end opposite the coupling tip, wherein the drive end is exposed from the inner lumen of the test stem when the connector shaft is received in the inner lumen.

12. The system of claim 1, wherein the prosthesis stem is adapted to be disposed in a medullary canal of a humerus to support an artificial humeral head.

13. The system of claim 1, wherein the mating feature of the reference anchor comprises a female receptacle, and wherein the terminal end of the stem comprises at least one male protrusion configured to mate with the female receptacle in the at least one discrete rotational orientation such that the stem is disposed in the desired rotational orientation in the bone cavity.

14. The system of claim 1, further comprising the connector shaft, wherein the connector shaft comprises a coupling tip adapted to mate with the mating feature of the reference anchor in the at least one discrete rotational orientation for positioning the reference anchor at a desired depth and the desired rotational orientation in the bone cavity, such that, when the connector shaft is mated with the reference anchor in the at least one discrete rotational orientation, rotation of the connector shaft causes rotation of the reference anchor thereby screwing the reference anchor into the inner surface of the bone cavity to facilitate positioning the mating feature of the reference anchor in the desired rotational orientation.

15. A system for securing a prosthesis in a bone, the system comprising:
    a reference anchor for insertion into a cavity of a bone to define a reference point during prosthesis implantation, the reference anchor including a body having a mating feature and a gripping portion for engaging an inner surface of the bone cavity, the gripping portion including external threads for threading the bone cavity;
    a connector shaft having a coupling tip adapted to mate with the mating feature of the reference anchor in at least one discrete rotational orientation for positioning the reference anchor at a desired depth and a desired rotational orientation in the bone cavity such that, when the connector shaft is mated with the reference anchor in the at least one discrete rotational orientation, rotation of the connector shaft rotates the reference anchor and screws the reference anchor into the inner surface of the bone cavity to facilitate positioning the mating feature at the desired depth and the desired rotational orientation; and a prosthesis stem having a terminal end adapted to mate with the mating feature of the reference anchor in the at least one discrete rotational orientation such that the prosthesis stem is disposed at the desired depth and the desired rotational orientation.

\* \* \* \* \*